US006800063B2

(12) United States Patent
Iwata

(10) Patent No.: US 6,800,063 B2
(45) Date of Patent: Oct. 5, 2004

(54) FOOT STIMULATION TOOL

(76) Inventor: Kazuo Iwata, 81-5 Hachiman aza Hosomi, Chita-city, Aichi (JP)

(*) Notice: Subject to any disclaimer, the term of this patent is extended or adjusted under 35 U.S.C. 154(b) by 39 days.

(21) Appl. No.: 10/131,571

(22) Filed: Apr. 25, 2002

(65) Prior Publication Data

US 2003/0187372 A1 Oct. 2, 2003

(30) Foreign Application Priority Data

Apr. 2, 2002 (JP) ....................................... 2002-099669

(51) Int. Cl.$^{7}$ ............................ A61F 5/01; A61L 15/08

(52) U.S. Cl. ............................ 602/23; 602/30; 602/75; 128/893; 600/15

(58) Field of Search .............................. 602/27, 23, 30, 602/28, 29, 65, 75; 128/893, 894; 600/15; 36/88, 9 R, 71, 140; 2/16, 22

(56) References Cited

U.S. PATENT DOCUMENTS

| | | | | |
|---|---|---|---|---|
| 1,566,063 A | * 12/1925 | Barry | .......................... | 602/30 |
| 1,899,092 A | * 2/1933 | Hogan | .......................... | 602/30 |
| 5,437,616 A | * 8/1995 | Kasahara | .......................... | 602/30 |
| 6,143,946 A | * 11/2000 | Docter | .......................... | 602/41 |
| 6,545,193 B1 | * 4/2003 | Morgenstern | .......................... | 602/41 |

FOREIGN PATENT DOCUMENTS

| | | |
|---|---|---|
| JP | 10-52472 | 2/1998 |
| JP | 11-169426 | 6/1999 |
| JP | 2001-087297 | 4/2001 |

* cited by examiner

*Primary Examiner*—Danton D. DeMille
(74) *Attorney, Agent, or Firm*—Parkhurst & Wendel, L.L.P.

(57) ABSTRACT

The space for putting round the toes 5 surrounded by the opposed edges 11 of the horizontal band pieces 1 and 2 and the cord for putting round the toes having contraction and expansion properties 4 is formed by linking between the upper ends of the opposed edges 11 of the pair of horizontal band pieces 1, 2 for right and left sides using the cord for putting round the toes having contraction and expansion properties 4 and by linking the lower ends of the horizontal band pieces 1 and 2 for right and left sides by the fasteners 3 or the like. Moreover, the section for putting round an ankle 12 is formed by linking the idler ends 10 and 10 of both the horizontal band pieces 1 and 2 each other by given means. The tip of the sole is positioned in the space for putting round the toes 5, the cord for putting round the toes having contraction and expansion properties 4 is put round between the big toe A and second toe B, the lower edges of the interior ends of the horizontal band pieces 1 and 2 are made in contact with the arch of the foot C, the rear sides of both the horizontal band pieces 1 and 2 are attached along with both sides of the foot, in addition to this, the outer end sides of the horizontal band pieces 1 and 2 linked to the ankle D are engaged and stopped, fitted it on the foot, and an appropriate stimulus is given between the big toe A and second toe B by the cord for putting round the toes having contraction and expansion properties 4.

7 Claims, 12 Drawing Sheets

FOOT STIMULATION TOOL

BACKGROUND OF THE INVENTION

1. Field of the Invention

The present invention relates to a foot stimulating healthy tool capable of facilitating blood circulation by giving an appropriate stimulus to the foot and alleviating muscle fatigue.

2. Description of the Related Art

Conventionally, as a foot stimulating healthy tool for stimulating the foot and promoting the health, what is called a bamboo foot massaging mat that the user steps on a mat with projections by soles of feet and the mat stimulates the soles of feet, a pair of sandals with projections for being put on and giving a stimulus to the soles of feet and the like are known.

However, it is difficult to hold on the stepping on the bamboo foot massaging mat as described above since it is monotonous, and a pair of sandals have a problem that pains accompany with it until the user accustoms himself/herself to putting on these because the whole body weight is added to the sole of the feet with which the projections are contacted.

SUMMARY OF THE INVENTION

Therefore, an object of the present invention is to provide a foot stimulating healthy tool capable of continuously giving an appropriate stimulus to feet without accompanying pains.

A foot stimulating healthy tool of the present invention is characterized in that it was made so that the foregoing foot stimulating healthy tool forms a space for putting around the toes surrounded by opposed edges of horizontal band pieces and a cord for putting around the toes having contraction and expansion properties described above by linking the lower ends of a pair of horizontal band pieces for right and left sides by means of given means, which have been linked between the upper ends of opposed edges by a cord for putting around the toes having contraction and expansion properties, and a section for putting around an ankle can be formed by linking free-ends of both horizontal band pieces together by given means.

A foot stimulation healthy tool of the present invention can facilitate blood circulation of feet only by the setting that the tip of the sole is positioned in the space for putting a cord around toes, a cord for putting around the toes having contraction and expansion properties is put between the big toe and second toe, the section for putting around an ankle is engaged and stopped at the ankle and it is set so as to fit on the feet, and an appropriate stimulus is always given to the portion between the big toe and second toe by tractive force of the cord for putting between the toes having contraction and expansion properties.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention, wherein.

DESCRIPTION OF THE PREFERRED EMBODIMENTS

Next, the preferred Examples of the present invention will be described in detail below.

Figure 1:
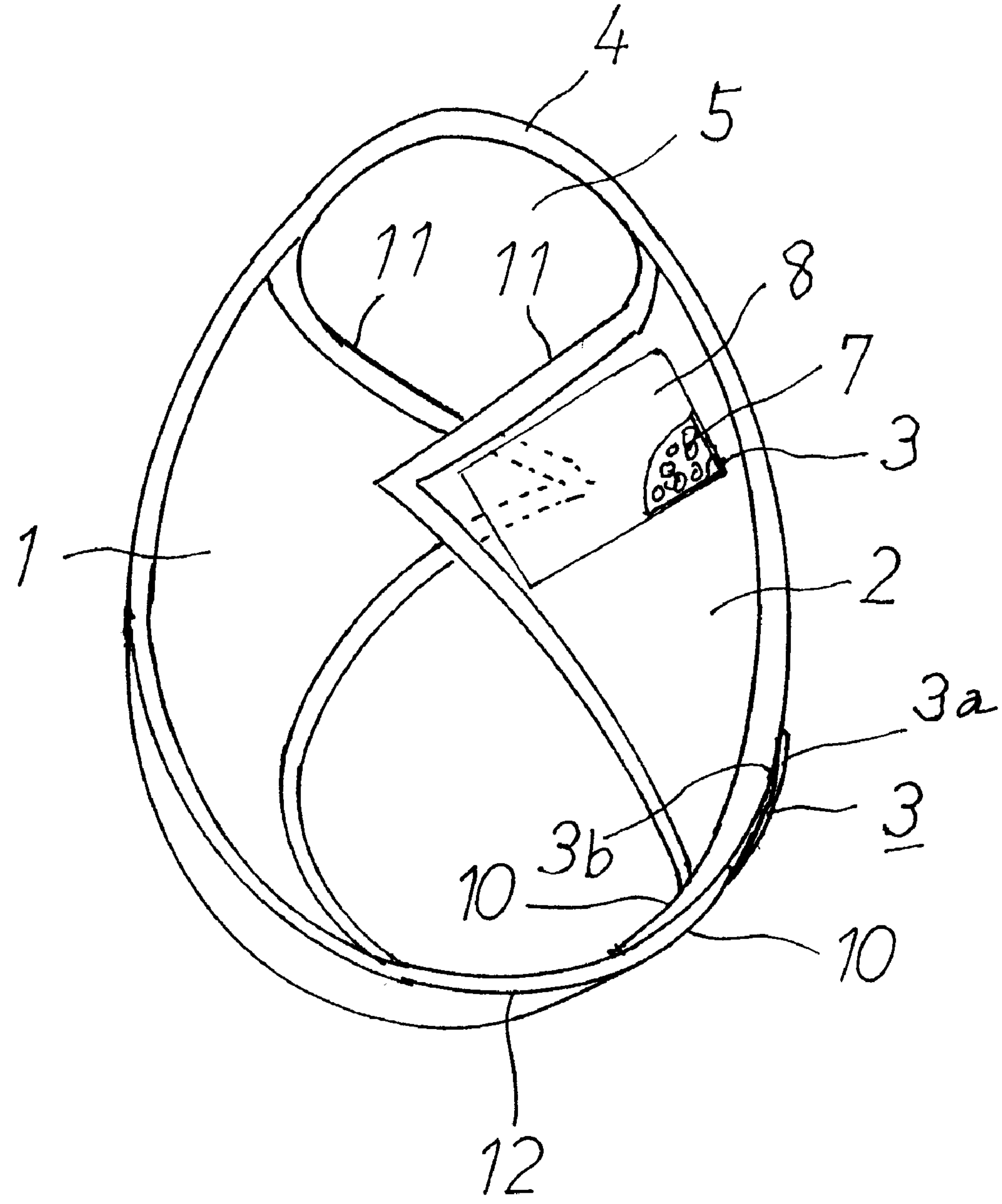
FIG. 1 is a plan view showing a foot stimulation healthy tool of the First Example.
Figure 2:
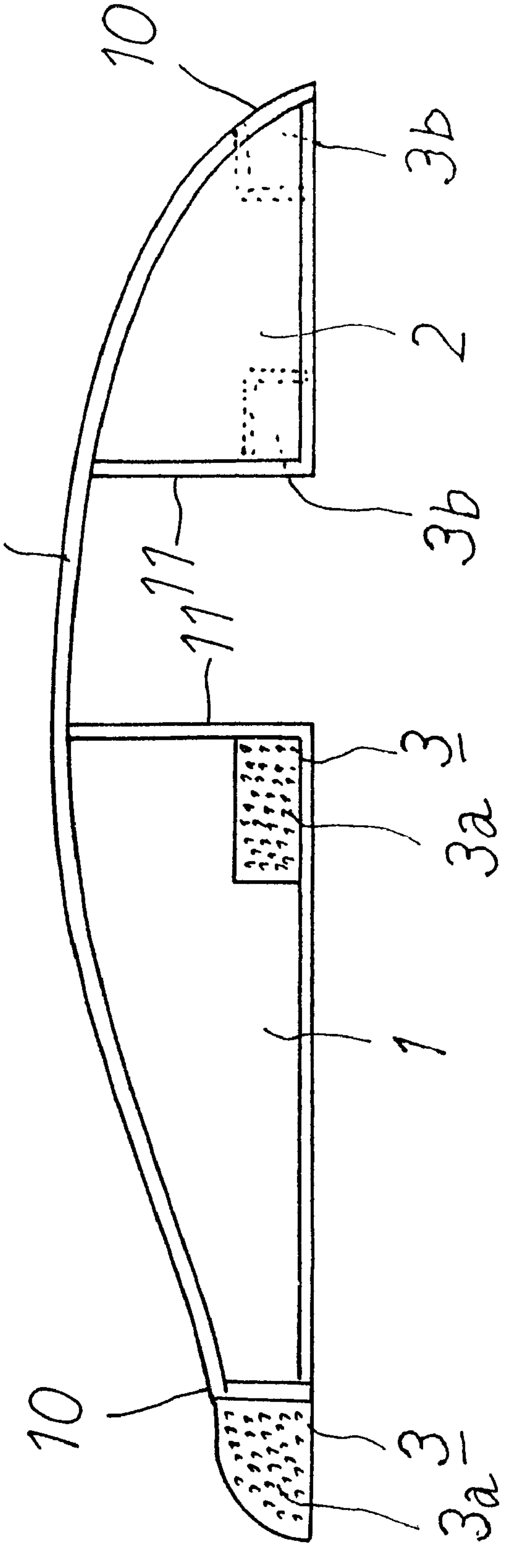
FIG. 2 is a development showing a foot stimulation healthy tool of the First Example.

In the First Example shown in FIG. 1 and FIG. 2, the reference numerals 1, 2 denote a pair of horizontal band pieces for right and left sides comprising a cloth or fabric having contraction and expansion properties. As for these horizontal band pieces 1, 2, one horizontal band piece 1 is longer than the other horizontal band piece 2, on its free ends 10, a fasteners 3 is provided as means for linking both. As to the fasteners shown in FIGS. 1 and 2, face fasteners are stitched as fasteners 3 for linking free ends 10 in a freely engaged and released manner, however, free ends 10 and 10 may be originally integrated by stitching these each other.

The pair of horizontal band pieces 1, 2 for right and left sides are arranged at the predetermined interval, are linked by the cord for putting between the toes having contraction and expansion properties 4 between the upper ends of the opposed edges 11, and it is made so that a space for putting between toes 5 surrounded by the opposed edges 11 of the horizontal band pieces 1 and 2 and the cord for putting between the toes having contraction and expansion properties 4 is formed by linking the lower ends of the opposed edges 11 each other by means of given linking means such as the fasteners 3 or the like as shown in FIG. 1. Moreover, as described above, it is made so that the section for putting around an ankle 12 is formed by linking the free ends 10 and 10 of both horizontal band pieces 1 and 2 each other with the fasteners 3, or by stitching and integrating it.

In the present Example, face fasteners are used as means for linking the free ends 10 and 10 of the horizontal band pieces each other in a freely engaged and released manner, while a hook face section 3*a* which is a male half is stitched on the outer end of the one horizontal band piece 1, a loop face section 3*b* which is a female half is stitched on the outer end of the other horizontal band piece 2. However, in the case where a raising cloth on which a loop is formed on the outer end surface is used as the horizontal band piece 2, it is not necessary to attempt to use the loop face section 3*b*.

As linking means for forming the space for putting between the toes 5 between the cord for putting between the toes having contraction and expansion properties 4 and the opposed edges 11 of the horizontal band pieces 1 and 2 linked each other, in the Example shown in FIG. 2, the fasteners 3 such as face fasteners or the like similar to means for linking the free ends 10 and 10 of the horizontal band pieces 1 and 2 in a freely engaged and released manner described above are used. In this case, while the hook face section 3*a* which is a male half is stitched on the lower edge side of inside surface of the interior end of the one horizontal band piece 1, a loop face section 3*b* which is a female half is formed similarly to the foregoing case, stitched on the lower edge side of inside surface of the interior end of the other horizontal band piece 2, both are made to be set in a freely engaged and released manner and the linking position is made to be set in a freely adjustable manner. As a result of this, it is made to be set in a freely adjustable manner corresponding to the largeness and shape of the foot of the person who wears it, however, the other kinds of fasteners may be used, and it may be made so that interior ends of the horizontal band pieces 1 and 2 each other is not set in a freely engaged and released manner but has been originally stitched and integrated.

In the present Examples, as shown in FIG. 1, a tourmaline 7 is incorporated in either of the foregoing horizontal band pieces 1 or 2, or both of these. The tourmalines 7 are attached in a freely engaged and released manner with the fasteners 3 at the required locations of the horizontal band pieces 1 and 2 as tourmaline stored in a cloth bag 8 in a powdered state or granular state, however, it may be directly stitched on the horizontal band pieces 1 and 2, and a net piece or cloth piece knitted and woven with the string which has been made by containing the tourmaline 7 may be attached by attaching and mounting it on the inside surfaces of the horizontal band pieces 1 and 2.

Figure 3:
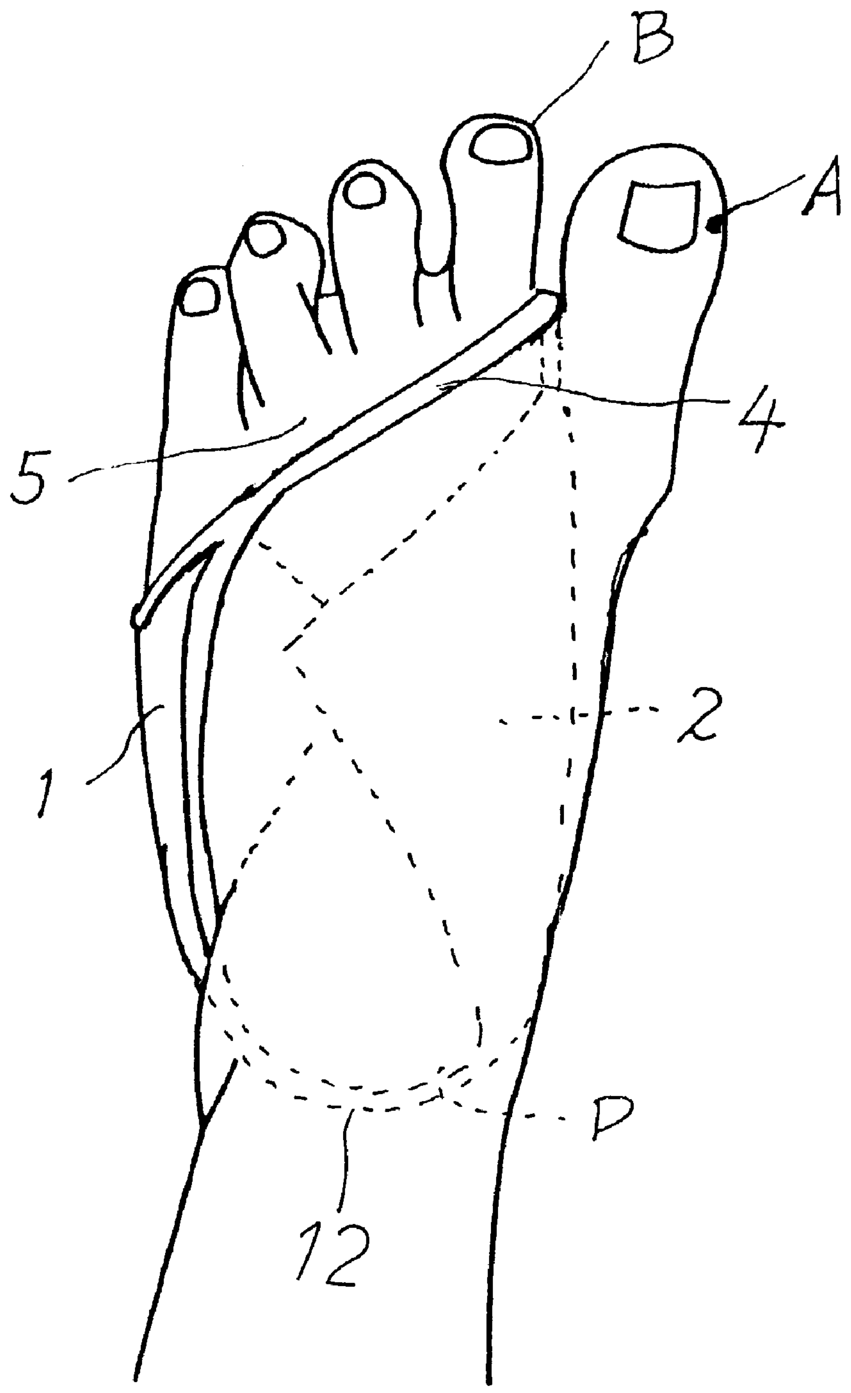
FIG. 3 is a plan view showing a state where a foot stimulation healthy tool of the First Example is fitted on the foot.
Figure 4:
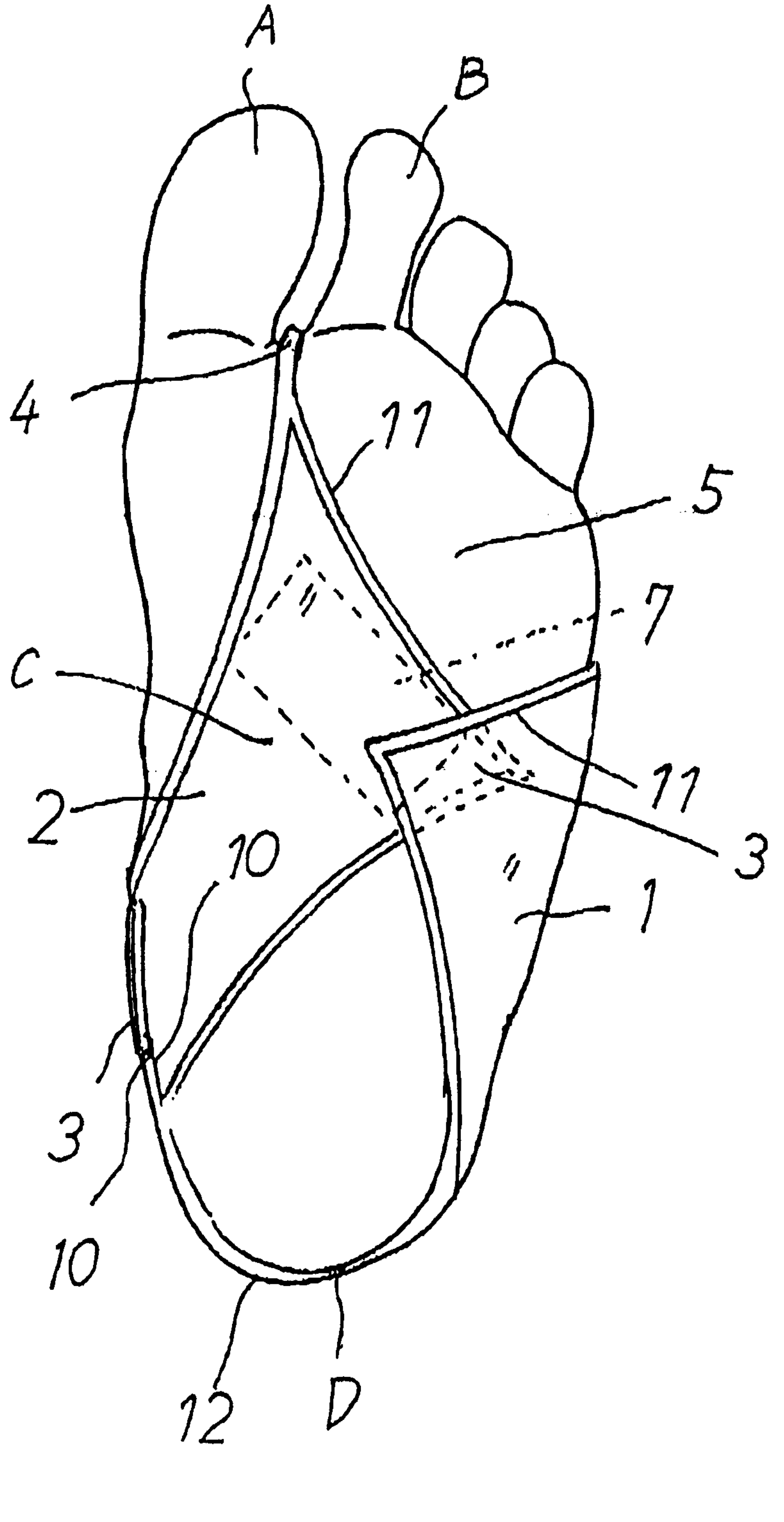
FIG. 4 is a bottom plan view showing a state where a foot stimulation healthy tool of the First Example is fitted on the foot.
Figure 5:
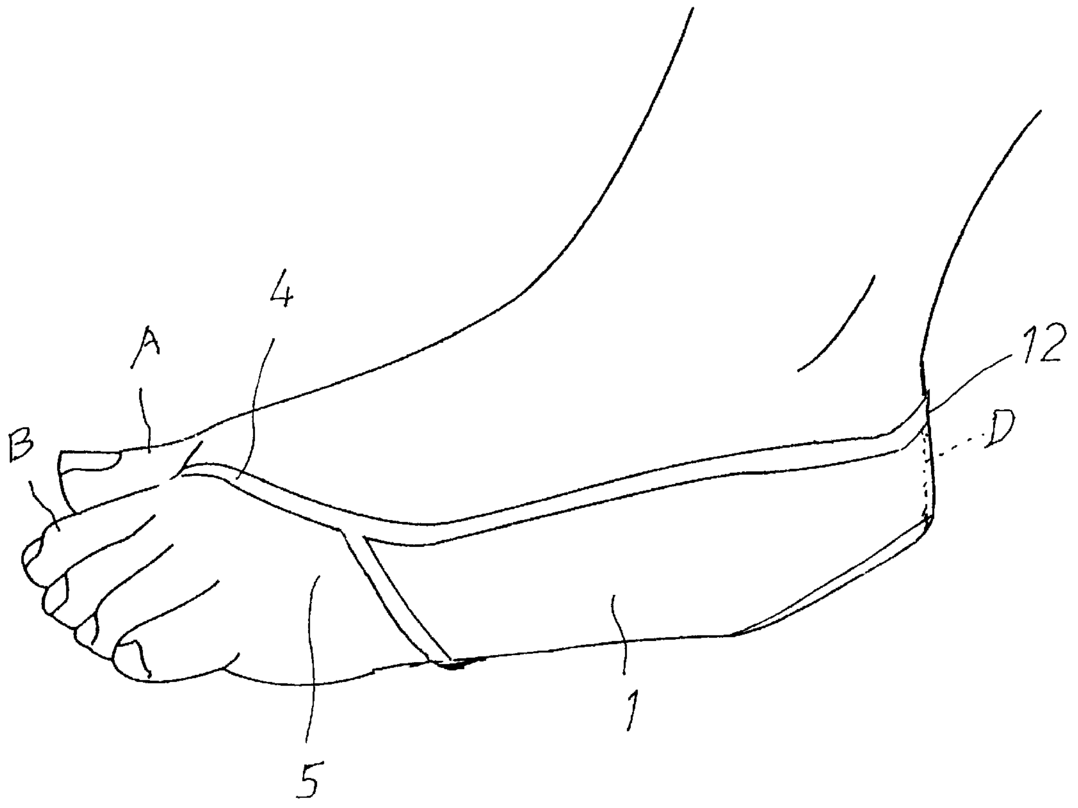
FIG. 5 is a side elevation view showing a state where a foot stimulation healthy tool of the First Example is fitted on the foot.

As shown in FIG. 3, FIG. 4, FIG. 5, as for a foot stimulating healthy tool of the present invention thus configured, the tip of the sole is positioned in the space for putting between the toes 5 surrounded by the opposed edges 11 of the horizontal band pieces 1 and 2, and the cord for putting between the toes having contraction and expansion properties 4, the cord for putting between the toes having contraction and expansion properties 4 is putted between the big toe A and second toe B, the lower ends of the opposed edges 11 which has been linked to the horizontal band pieces 1 and 2 is attached to and in contact with the arch of the foot C. Moreover, end sides of both the horizontal band pieces 1 and 2 are attached along with the both sides of the foot, and then, the free ends 10 and 10 of the horizontal band pieces 1 and 2 are linked each other with the fasteners 3, or the section for putting around the ankle 12 linked as one stitched and integrated together is engaged and stopped at the ankle D. If it is thus fitted on the foot, an appropriate stimulus is given the portion between the big toe A and second toe B by a tractive force of the cord for putting between the toes having contraction and expansion properties, the blood circulation is improved when the user moves the muscles.

In this case, accordingly, the cord for putting between the toes having contraction and expansion properties 4 pulls both the horizontal band pieces 1 and 2, therefore, it gives a stimulus to the arch of the foot C, both sides of the foot and the ankle by comfortable pressure. Moreover, since the locations except for the instep and sole are not pressurized from the horizontal band pieces 1 and 2, it becomes in a putting on state with a librating feeling, there is no fear of the user suffering from blood stasis. Moreover, the big toe A is pressurized towards inside by widening the portion between the big toe A and second toe B by means of the cord for putting between the toes having contraction and expansion properties 4, and both the horizontal band pieces 1 and 2 pressurize both sides, therefore, these interactions result in the prevention of hallux valgus.

Moreover, as to this foot stimulating healthy tool, the user is capable of wearing a pair of shoes while putting it on and is capable of living a usual life while putting it on. The entire toes are bent beneath by the cord for putting between the toes having contraction and expansion properties 4 being putted between the big toe A and second toe B when it is fitted on, even if it is in a state where the user wears a pair of shoes, the walking during which the sole suitably and precisely makes use of the toes within the pair of shoes is performed, accordingly, the walking can be performed without loading to hip and legs and without fatigue. Moreover, the bridge of the arch of the foot is maintained by bending the entire toes beneath, in addition to this, the cord for putting between the toes having contraction and expansion properties 4 contracts and expands, then gives a stimulus while changing the pressurized forces and makes the muscles of the feet excise by the movements of the feet accompanying with the walking, it further promotes the blood circulation without fatigue.

Moreover, as shown in FIG. 1, if the tourmaline 7 were previously incorporated on the horizontal band pieces 1 and 2, since weak current and far infrared ray are generated by receiving the pressure accompanying with the walking and by heating due to the body temperature, what is called a therapeutic point of the foot receives a stimulus owing to these, and further promotes the regeneration and metabolism of the body. It should be noted that if the tourmaline 7 is mounted on both the horizontal band pieces 1 and 2 stored in a powdered or granular state within the cloth bag 8 with which the arch of the foot is in contact, weak current and far infrared ray are further generated by adding one portion of the body weight, that is, that pressurizing on the tourmaline within the cloth bag 7 during the walking, the extremely excellent effects are exerted, particularly, if the tourmaline is made in a granular state, it has also the effect that the tourmaline strikes the arch of the foot as particle projections and stimulates the arch of the foot, along with the above-described effect. Furthermore, if the net pieces or cloth pieces woven by strings containing the tourmaline 7 are attached and mounted inside of the horizontal band pieces 1 and 2, it is preferable because the tourmaline 7 can be easily attached on any of the inside surfaces of the horizontal band pieces 1 and 2.

Figure 6:
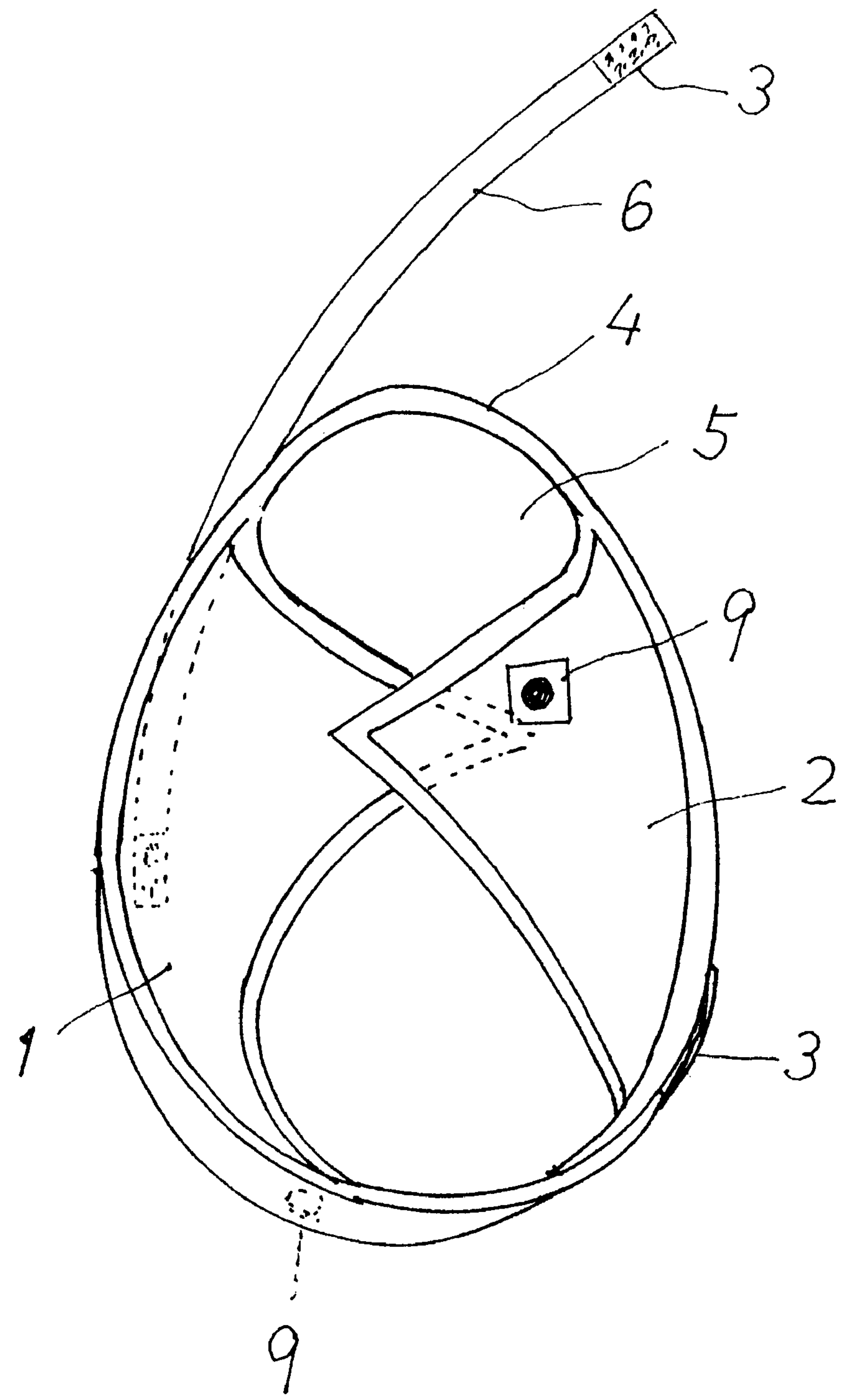
FIG. 6 is a plan view showing a foot stimulation healthy tool of the Second Example.
Figure 7:
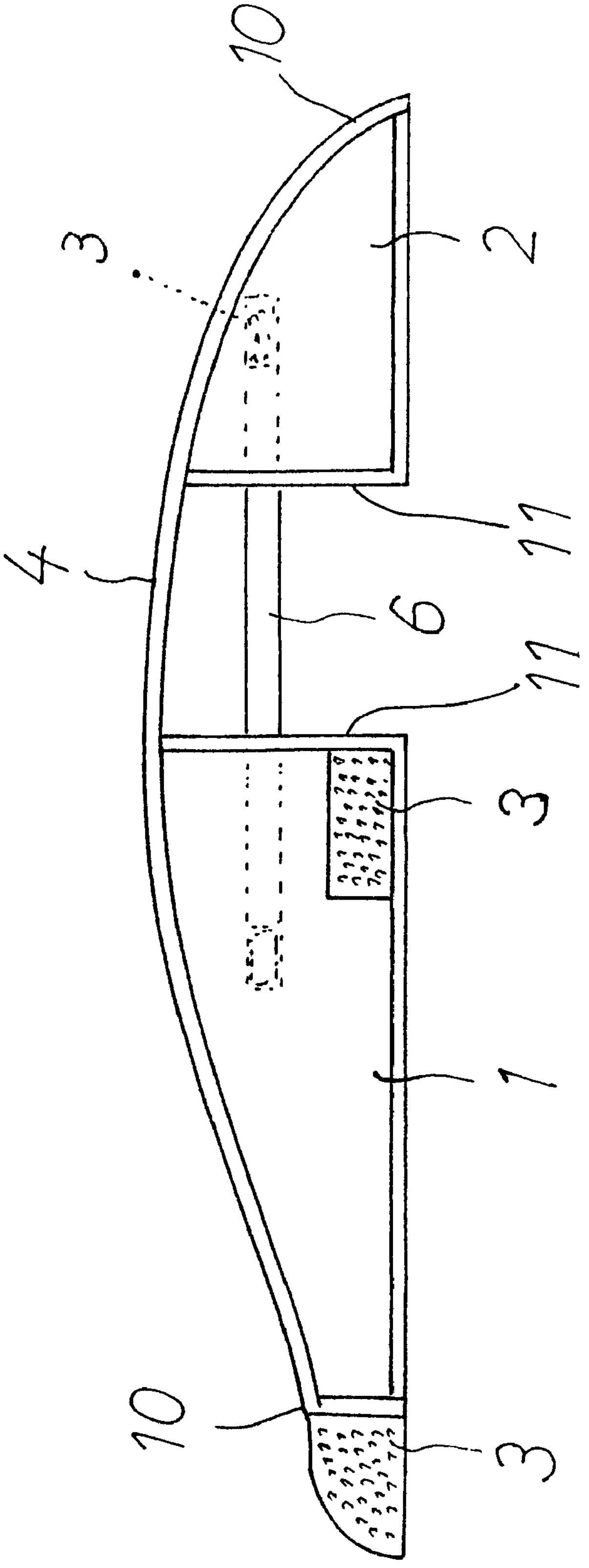
FIG. 7 is a development showing a foot stimulating healthy tool of the Second Example.

FIG. 6 and FIG. 7 show the Second Example, in which both ends of the auxiliary band having contraction and expansion properties 6 are attached on the horizontal band pieces 1 and 2 for right and left sides. As for the auxiliary band having contraction and expansion properties 6 shown in FIGS. 6 and 7, one of the end portions is set in a freely attachable and detachable manner by the fasteners 3, and the other end portion is stitched, however, both the end portions may be stitched or both the end portions may be set in a freely attachable and detachable manner by the fasteners 3. Moreover, as shown in FIG. 6, in the present Example, a magnet 9 is mounted on either the horizontal band piece 1 or 2, or both of these by given means such as stitching, adhering and the like. The magnet 9 has an effect of alleviating stiff muscles by its magnetism. It should be noted that the magnet 9 might be selectively incorporated with the tourmaline using the fasteners.

Figure 8:
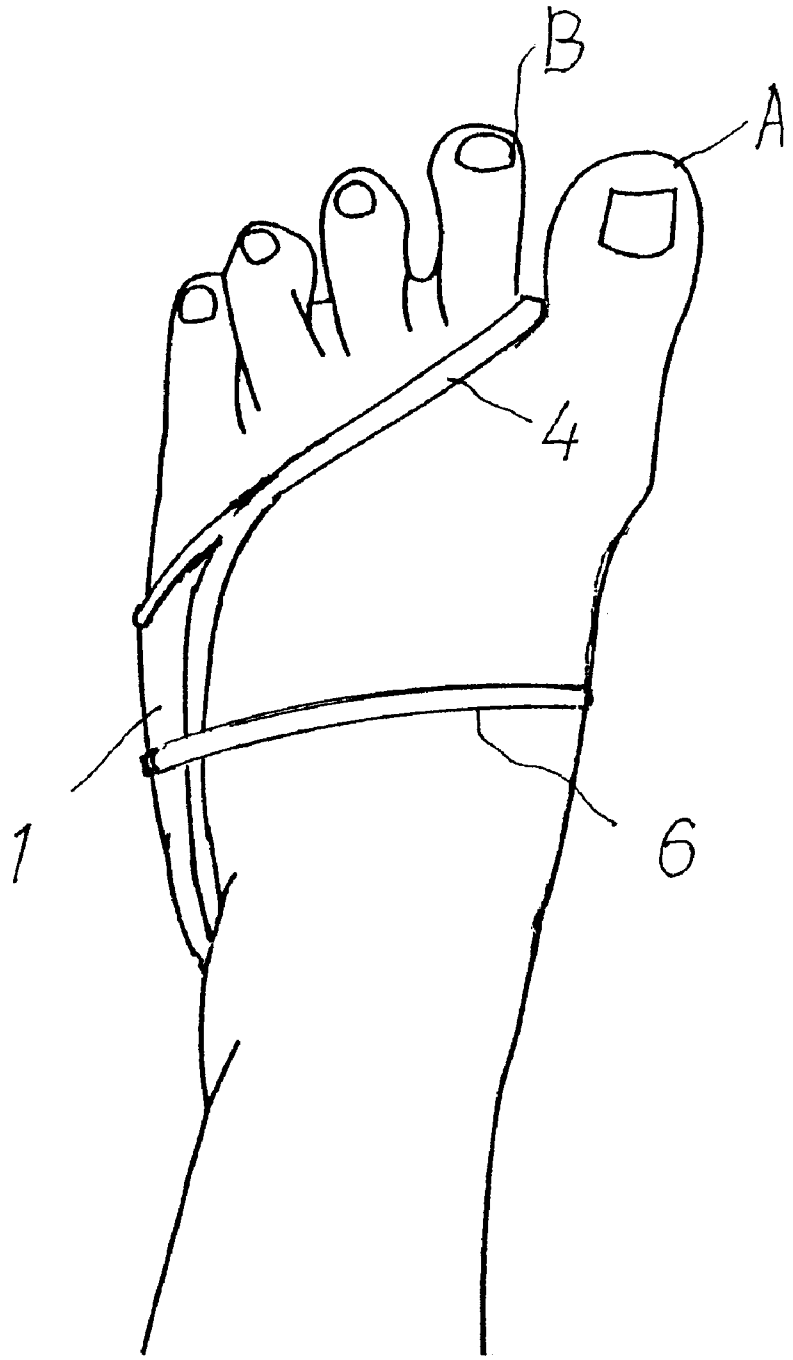
FIG. 8 is a plane view showing a state where a foot stimulating healthy tool of the Second Example is fitted on the foot.
Figure 9:
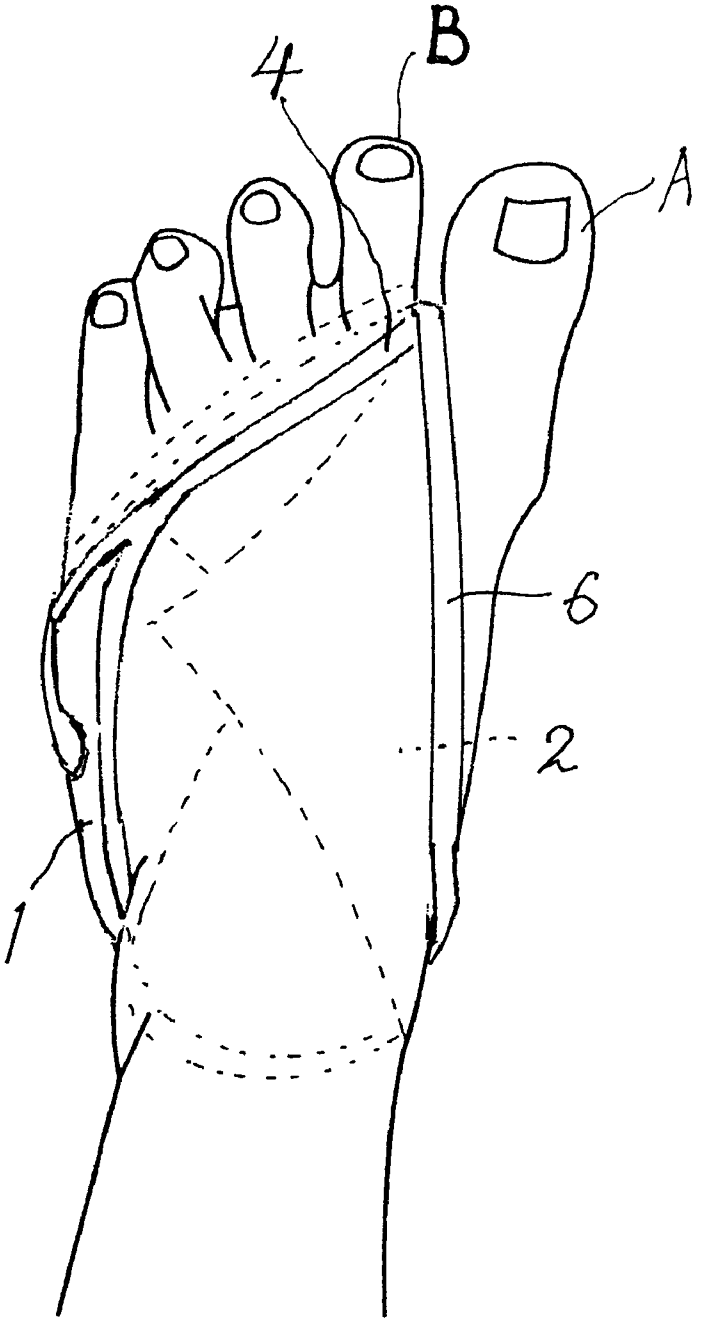
FIG. 9 is a plane view showing a state where a foot stimulating healthy tool of the Second Example is fitted on the foot by the other method.

As shown in FIG. 8, if the auxiliary band having contraction and expansion properties 6 is fitted on so that it wraps around the instep of the foot, there is no fear that the horizontal band pieces 1 and 2 are released from the foot, and as shown in FIG. 9, the releasing of the horizontal band pieces 1 and 2 from the foot can be prevented as well as the stimulus stimulating the portion between the big toe A and second toe B is further strengthened by putting between the big toe A and second toe B similarly to the cord for putting between the toes having contraction and expansion properties 4 from the opposite side of the foot side portion of the relevant cord for putting between the toes having contraction and expansion properties. It should be noted that as shown in FIG. 6, one of the end sections of the auxiliary band having contraction and expansion properties 6 is set in a freely attachable and detachable manner by the fasteners 3 and the other end section is stitched, the auxiliary band having contraction and expansion properties 6 is neither released nor lost.

Figure 11:
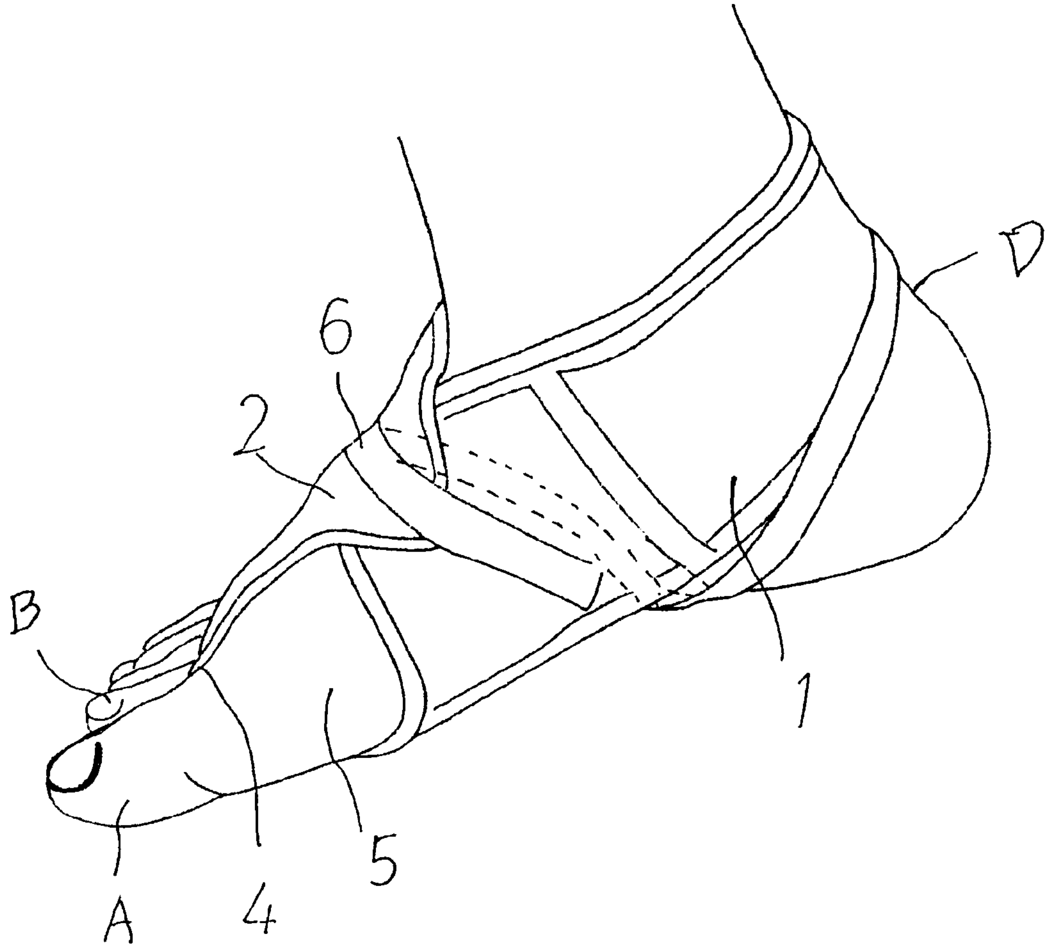
FIG. 11 is a perspective view showing the other method for fitting a foot stimulating healthy tool of the Second Example on the foot.
Figure 12:
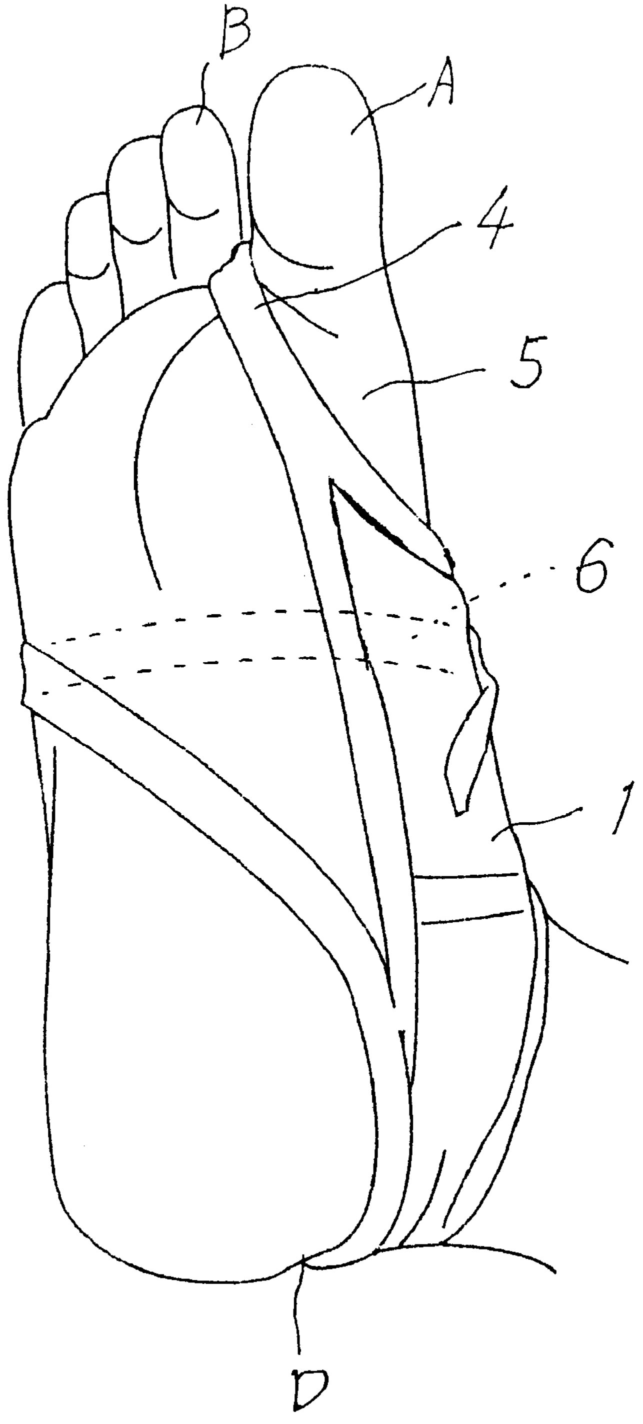
FIG. 12 is a perspective view showing the other method for fitting a foot stimulating healthy tool of the Second Example on the foot.

Next, the other method for wearing a foot stimulating healthy tool of the present invention will be described with reference to FIG. 10 through FIG. 12. The method for wearing is different from the foregoing method for wearing, in which the horizontal band pieces 1 and 2 are in contact with the instep of the foot, the free ends 10 and 10 of the horizontal band pieces 1 and 2 are linked each other by the fasteners 3, or the section for putting around the ankle 12 linked as integrated one by stitching is set in an engaged and stopped state at the ankle D, and the tip of the sole is positioned in the space for putting between the toes 5 surrounded by the opposed edges of the horizontal band pieces 1 and 2 and the cord for putting between the toes having contraction and expansion properties 4, and it is fitted on by putting the cord for putting between the toes having contraction and expansion 4 between the big toe A and second toe B.

Figure 10:
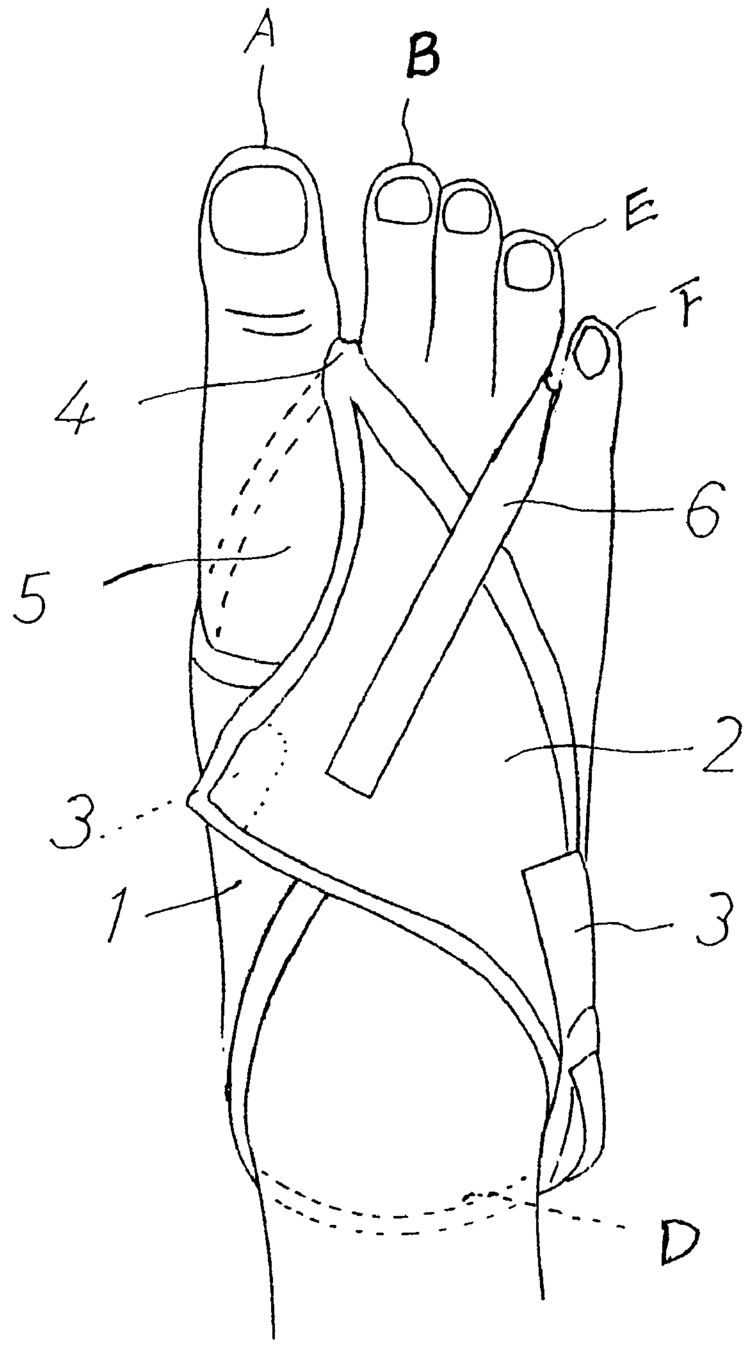
FIG. 10 is a plan view showing the other method for fitting a foot stimulating healthy tool of the Second Example on the foot.

Moreover, as for a foot stimulating healthy tool in which the auxiliary band having contraction and expansion properties 6 is provided as shown in FIGS, the auxiliary band having contraction and expansion properties 6 is put between the third finger E and little toe F as shown in FIG. 10, and it can give a stimulus to this location, too. Furthermore, as shown in FIG. 11 and FIG. 12, if it is fitted on so that it wraps around the instep of the foot, the horizontal band pieces 1 and 2 are adhered to the foot, gives a comfortable stimulus and there is no fear of its releasing from the foot.

According to this method for wearing, since the horizontal band pieces 1 and 2 are not in contact with the sole, the user gets barefoot feeling on the sole and the force is easily added to the sole, and in the case of enjoying the sports, it is the most suitable form. Moreover, since the horizontal band pieces 1 and 2 are not in contact with the sole, if a person who intends to wear it is flatfooted, that is, even if the arch of the foot is not formed on his or her sole, it is advantageous that it can be fitted on. It should be noted that the other effects by this method for wearing is similar to the method for wearing described above.

As described above, a foot stimulating healthy tool of the present invention can give a comfortable stimulus to the feet by routinely putting it on the feet.

It will also be appreciated that, although a limited number examples of the invention have been described in detail for purposes of illustration, various modifications may be made without departing from the spirit and scope of the invention. Accordingly, the invention should not be limited except as by the appended claims.

What is claimed is:

1. A foot stimulation tool comprising:

first and second horizontal band pieces each having a free end and a linking end;

a releasable fastener comprising cooperating fastening portions mounted on each of said first and second horizontal band pieces; and an elastic cord attached to the linking ends and having a length extending between the first and second horizontal band pieces, wherein the length of said elastic cord is for extending between two toes of a person wearing said tool and for developing a tractive force toward a root of the toes, said first horizontal band for extending across the sole of a foot of a person wearing said tool from a first side to a second side of the sole, said second horizontal band for wrapping around a side of the foot and extending across the sole from a second side to a first side of the sole and overlapping the first horizontal band, said overlapping bands for being linked together by said releasable.

2. The foot stimulation tool according to claim 1, wherein said cooperating fastening portions are mounted to at least one end of each of said horizontal band pieces.

3. The foot stimulation tool according to claim 1, wherein said first and second horizontal bands further comprise a section for wrapping round an ankle of a person wearing the tool.

4. The foot stimulation tool according to claim 1, further comprising an auxiliary elastic band having two ends each attached to a respective one of said horizontal band pieces.

5. The foot stimulation tool according to claim 1, further comprising tourmaline mounted on at least one of said horizontal band pieces.

6. The foot stimulation tool according to claim 5, further comprising a cloth bag, and wherein is contained in said cloth bag in a powdered or granular state, and said cloth bag is releasably attached to said horizontal band by said releasable fastener.

7. The foot stimulation tool according to claim 1, further comprising a magnet mounted on at least one of said horizontal band pieces.

* * * * *